United States Patent [19]

Brown et al.

[11] Patent Number: 4,556,561

[45] Date of Patent: Dec. 3, 1985

[54] COMPOSITIONS AND METHODS FOR TOPICALLY FLUORIDATING AND/OR MINERALIZING DENTAL TISSUE

[75] Inventors: Walter E. Brown, Rockville; Laurence C. Chow, Gaithersburg, both of Md.

[73] Assignee: American Dental Association Health Foundation, Washington, D.C.

[21] Appl. No.: 698,314

[22] Filed: Feb. 5, 1985

Related U.S. Application Data

[63] Continuation of Ser. No. 478,888, Mar. 25, 1983, abandoned.

[51] Int. Cl.[4] .................. A61K 7/18; A61K 33/16; A61K 33/42
[52] U.S. Cl. ....................... 424/151; 424/48; 424/49; 424/52; 424/57; 424/128
[58] Field of Search ............... 424/52, 57, 128, 151

[56] References Cited

U.S. PATENT DOCUMENTS

| | | | |
|---|---|---|---|
| 3,337,412 | 8/1967 | Elbreder | 424/128 |
| 4,048,300 | 9/1977 | Tomlinson et al. | 424/57 |
| 4,080,440 | 3/1978 | Digiulio et al. | 424/57 |
| 4,083,955 | 4/1978 | Grabenstetter et al. | 424/57 |
| 4,097,588 | 6/1978 | Levine | 424/57 |
| 4,108,980 | 8/1978 | Duff | 424/57 |
| 4,139,599 | 2/1979 | Tomlinson et al. | 424/57 |
| 4,177,258 | 12/1979 | Gaffar et al. | 424/57 |
| 4,183,915 | 1/1980 | Gaffar et al. | 424/57 |
| 4,198,394 | 4/1980 | Faunce | 424/57 |
| 4,267,167 | 5/1981 | Weitzman et al. | 424/52 |

OTHER PUBLICATIONS

Brandao CA. 86: 83872k (1977); Levine C.A. 87: 58534q (1977); Feagin C.A. 79# 111621d; Duff CA. 74: 46349b (1971); Tomlinson et al., CA. 82: 175232x (1975); Duff CA. 82: 35055s (1975); Purdell-Lewis CA. 91: 151170k (1979); Kirkegaard CA. 86: 114966a (1977); Jordan CA. 74: 139024g (1971).

*Primary Examiner*—Shep K. Rose
*Attorney, Agent, or Firm*—Allegretti, Newitt, Witcoff & McAndrews, Ltd.

[57] ABSTRACT

Solutions, gels, and substantially nonaqueous dispersions that form dicalcium phosphate dihydrate under appropriate conditions are disclosed, as well as methods for their use. These compositions are useful in topically fluoridating and/or mineralizing dental tissue, such as enamel, dentin, and exposed root surfaces. The incorporated fluoride is in the form of $Ca_5(PO_4)_3F$ and is more permanently retained than $CaF_2$ and other fluoridation products.

7 Claims, No Drawings

COMPOSITIONS AND METHODS FOR TOPICALLY FLUORIDATING AND/OR MINERALIZING DENTAL TISSUE

This is a continuation of copending Application Ser. No. 478,888, filed Mar. 25, 1983, now abandoned.

BACKGROND OF THE INVENTION

1. Field of the Invention

This invention was made during research supported in part by a grant from the National Institute of Dental Research. The present invention relates to compositions and methods for topically fluoridating and/or mineralizing dental tissue, such as enamel, dentin, and exposed root surfaces.

2. Background of the Invention

Topical fluoridation of teeth has been extensively used in the past three decades in attempts to reduce the incidence and severity of dental caries. See Newbrun, E. (ed.): *Fluorides and Dental Caries*, 2d ed., Springfield, IL: C. C. Thomas (1975); Keyes, P. H. et al, "Fluoride Therapy in the Treatment of Dentomicrobial Plaque Diseases." J. Am. Soc. Preventive Dentistry 5:17–26 (1975); Brudevold, F. et al, "A Study of Acidulated Fluoride Solutions-I In vitro Effects on Enamel." Archs. oral Biol. 8:167–177 (1963). The typical procedure introduces simple fluoride containing compounds onto the surface of the dental enamel. This produces a relatively large and immediate fluoride uptake in the enamel. Most of this fluoride, however, is present in the form of $CaF_2$ and quickly leaches out of the enamel. Thus, typical topical fluoridation treatments result in little or no long-term increase in enamel-bond fluoride content, and can actually cause a net loss of tooth mineral and fluoride content. See, McCann, H. G., "The Solubility of Fluorapatite and Its Relationship to That of Calcium Fluoride." Archs. oral Biol. 13:987–1001 (1968); Heiftz, S. B. et al, "In vivo Fluoride Uptake by Enamel of Teeth of Human Adults from Various Topical Fluoride Procedures." Archs. oral Biol. 15:1171–1181 (1970); Wei, S. H. Y. et al, "In Vivo Microsampling of Enamel Fluoride Concentration After Topical Treatments." Caries Res. 9:50–58 (1975) Chow, L. C. et al, "Apatitic Fluoride Increase in Enamel from a Topical Treatment Involving Intermediate $CaHPO_4.2H_2O$ Formation, an In vivo Study." Carries Res. 15:369–379 (1981). Since both ambient and enamel-bound fluoride appear necessary to combat caries (see Brown, W. E. et al (eds.), "Cariostatic Mechanisms of Fluorides," Caries Res. 11 (suppl. 1)1–327 (1977)), it appears that the short-lived, beneficial effects of most known topical fluoride treatments are due to a temporary elevation in the ambient fluoride level in the mouth. The inability to incorporate fluoride into the enamel crystals appears to be the major reason behind the limited effectiveness of these topical fluoride treatments.

A significant step in topical fluoridation was made by the present inventors in discovering that $CaHPO_4.2H_2O$, dicalcium phosphate dihydrate (DCPD), reacts rapidly with fluoride to form fluorapatite, $Ca_5(PO_4)_3F$, under appropriate conditions. Thus, conventional fluoride treatments can incorporate significant amounts of fluorapatite into dental enamel if DCPD is first formed in the enamel as an intermediate product. In general, DCPD will form in dental enamel from solutions at ambient temperatures that contain calcium and phosphate ions in concentrations approaching saturations with respect to DCPD and having a pH less than or equal to approximately 4.3, which is the pH of a solution saturated with respect to both DCPD and $Ca_5(PO_4)_3OH$, hydroxyapatite, in which both compounds are in equilibrium with the saturated solution at an ambient temperature. Such a pH is referred to as a singular point pH. In solutions at ambient temperatures with a pH above approximately 4.3, hydroxyapatite will precipitate rather than DCPD. See, Chow, L. C. and Brown, W. E., "The Reaction of Dicalcium Phosphate Dihydrate With Fluorides." J. Dent. Res. 52:1220–1227 (1973); Chow, L. C. and Brown, W. E., "Formation of $CaHPO_4. 2H_2O$ in Tooth Enamel as an Intermediate Product in Topical Treatments." J. Dent. Res. 54: 65–76 (1975); see also, Brown, W. E., "Solubilities of Phosphates and Other Sparingly Soluble Compounds," in Griffith, E. J. et al (eds.), *Environmental Phosphorus Handbook*, New York: John Wiley and Sons (1973). A solution that can react with hydroxyapatite or tooth mineral to form DCPD may be called a "DCPD-forming solution". The present inventors have also shown that highly acidic, saturated solutions of $Ca(H_2PO_4)_2.H_2O$, monocalcium phosphate monohydrate (MCPM), will form DCPD in solution under appropriate conditions. See Chow, L. C. and Brown, W. E., "Phosphoric Acid Conditioning of Teeth for Pit and Fissure Sealants." J. Dent. Res. 52:1158 (1973); Chow, L. C. and Brown, W. E., "Topical Fluoridation of Teeth Before Sealant Application," J. Dent. Res. 54:1089 (1975).

The fluoride compound incorporated into the enamel by DCPD-forming solutions is identified as fluorapatite because previous in vitro studies show that fluorapatite forms when DCPD reacts with a relatively dilute fluoride solution. See, Chow, L. C. and Brown, W. E., "The Reaction of Dicalcium Phosphate Dihydrate with Fluorides." J. Dent. Res. 52:1220–1227 (1973); Chow, L. C. and Brown, W. E., "Formation of $CaHPO_4. 2H_2O$ in Tooth Enamel as an Intermediate Product in Topical Treatments." J. Dent. Res. 54:65–76 (1975); and Wei, S. H. Y. et al, "Reactions of Dicalcium Phosphate Dihydrate with Fluoride Solutions." J. Dent. Res. 53:1145–1154 (1974). Because the primary components of tooth mineral are fluorapatite and hydroxyapatite, $Ca_5(PO_4)_3OH$, the incorporation of additional fluorapatite into dental enamel can, in effect, remineralize demineralized tooth material. This is especially helpful in combating the demineralization of the enamel's subsurface that precedes the onset of dental caries or cavities. Since the presence of fluoride ions prevents or retards tooth decay, the use of DCPD-forming solutions in conjunction with fluoridation agents both prevents dental caries and repairs incipient damage that might already have occurred. This combination of prevention and restoration is far more desirable than the conventional filling of cavities.

Studies with animals (Shern, R. J. et al, "Effects of Sequential Calcium Phosphate Fluoride Rinses on Fluoride Uptake in Rats." J. Dent. Res. 58(supp. B):1023 (1979); Brown, W. E. et al, "Animal Studies of Fluoride Penetration Procedure." IADR Program and Abstracts of Papers, No.827 (1978)), as well as a recent clinical study (Chow, L. C. et al, "Apatitic Fluoride Increase in Enamel from a Topical Treatment Involving Intermediate $CaHPO_4.2H_2O$ Formation, an In vivo Study." Caries Res.: 15:369–376 (1981)) show that treatment of dental enamel with solutions that form DCPD followed by treatment with a conventional fluoride source increases the permanently bound enamel fluoride content. It appears that the apatitic fluoride forms slowly in the enamel, since the reaction between DCPD and fluoride proceeds much longer than the treatment time per se. See, Chow, L. C. et al, "Reactions of Powdered Human Enamel and Fluoride Solutions With and Without Intermediate CaHPO$_4$.2H$_2$O Formation." J. Dent. Res. 59:1147–1452 (1980). Thus the formation of CaF$_2$ in the enamel after DCPD has been formed can improve the effectiveness of the treatment.

SUMMARY OF THE INVENTION

The present inventors have recently found that a fluoride-free DCPD-forming solution dissolves significant amounts of fluorapatite from the tooth surface if the tooth is not immediately treated with a fluoride agent. Thus, the known DCPD-forming solutions will reduce the enamel-bound fluoride content, a decidedly undesirable effect, if not immediately followed by fluoride treatment. Thus, there is a need for a DCPD-forming solution that will not remove fluorapatite from treated enamel.

A further problem with the known DCPD-forming solutions is that they necessarily require a two-step procedure—application of the DCPD-forming solution followed by application of the fluoridation agent. A one-step method would save a considerable amount of the patients' time and money by reducing costly dental chair time. A one-step treatment would also be more acceptable to dental clinicians. But because all DCPD-forming solutions contain relatively high concentrations of calcium ions, it is not possible to add the simple fluoride compounds present in conventional fluoridation agents into the DCPD-forming solution without causing massive precipitation of calcium fluoride, CaF$_2$. This precipitation not only removes calcium from the solution that would otherwise be available to remineralize the enamel, but it also reduces the fluoride concentration of the solution to a negligible amount. The result is a drastic reduction in remineralization and flouridation capacity. Thus, there is a need for a DCPD-forming solution that can fluoridate teeth in a one-step application without causing excessive precipitation of calcium fluoride.

Additionally, the known topical fluoridation prior art does not disclose any solid components that produce a DCPD-forming solution or gel upon contact with water. Such stable solids would be very advantageous for applications in nonaqueous media, such as toothpaste, chewing gum, mouthrinse, or gels for tray, bite block, and dental floss applications, and would permit home fluoridation and mineralization treatments. When DCPD is dissolved in water or nonacidic aqueous solvents at ambient temperatures, the resulting solution has a pH well above 4.3. Thus, a solution of DCPD in water will not form any DCPD in tooth enamel. Similarly, as shown by Pickel et al, "The Effects of a Chewing Gum Containing Dicalcium Phosphate on Salivary Calcium and Phosphate." J. Ala. Med. 2: 286–287 (1965), DCPD-containing chewing gum causes only temporary increases in salivary calcium and phosphate concentrations and no formation of DCPD in the enamel. This is because the pH of the resulting solution of DCPD and saliva is above 4.3, the singular point pH. Therefore, there is a need for solids that will produce DCPD upon contact with a dilute aqueous solvent, such as water or saliva.

An advantage of the present invention is that it provides compositions and methods for topically fluoridating and/or mineralizing dental tissue without dissolving fluorapatite from the tooth when the DCPD-forming solution or gel is applied to the tooth without immediately being followed by a fluoride treatment.

Another advantage of the present invention is that it provides compositions and methods for topically fluoridating and/or mineralizing dental tissue in a single step by slowly releasing free fluoride ions so that an excessive amount of calcium fluoride is not precipitated from the treatment solution or gel and the CaF$_2$ that is formed derives its calcium from the treatment solution and not from the tooth.

A further advantage of the present invention is that it provides compositions and methods for topically fluoridating and/or mineralizing dental tissue that comprise solid components that yield a DCPD-forming solution or gel upon contact with a dilute aqueous solvent, such as water or saliva.

The present invention provides compositions and methods for topically fluoridating and/or mineralizing dental tissue by treating the surface of the tissue with an aqueous solution or gel containing DCPD, CaHPO$_4$, (dicalcium phosphate anhydrous, DCPA), MCPM, or Ca(H$_2$PO$_4$)$_2$, (monocalcium phosphate anhydrous, MCPA), or a mixture or mixtures thereof, such that DCPD is formed in the treated surface of the tissue. The above phosphate compounds are present in the solution or gel with calcium and phosphate concentrations greater than or equal to approximately fifty percent of the concentrations necessary to saturate the aqueous solution or gel with respect to the phosphate compounds(s), and the pH of the solution or gel is less than or equal to the singular point pH of DCPD and hydroxyapatite at ambient temperatures, i.e., less than or equal to approximately 4.3. Furthermore, the solution or gel is saturated with respect to either fluorapatite or calcium fluoride. The presence of these simple fluoride compounds in dissolved form prevents the solution or gel from dissolving fluorapatite from the tooth surface even if a subsequent fluoride treatment is omitted. However, the application of this inventive DCPD-forming solution or gel should preferably be followed at some point by the application of an external fluoridation agent to the treated surface of the tissue such that fluorapatite is incorporated into the tissue. Alternatively, the sequence can be reversed such that the fluoridation agent is applied first followed by the DCPD-forming solution. As a third possibility, the fluoridation step and DCPD-forming step may be performed simultaneously.

The inventive topical fluoride treatment procedures may be illustrated by the following equations:

$$\text{Ca}_5(\text{PO}_4)_3\text{OH (tissue)} + \quad (1)$$

$$2\text{Ca}(\text{H}_2\text{PO}_4)_2 \text{ (DCPD-forming solution)} +$$

$$13\text{H}_2\text{O} = 7\text{CaHPO}_4.2\text{H}_2\text{O (solid)}$$

$$7\text{CaHPO}_4.2\text{H}_2\text{O} + \tfrac{7}{5}\text{F}^- = \tfrac{7}{5}\text{Ca}_5(\text{PO}_4)_3\text{F} + \quad (2)$$

$$\tfrac{14}{5}\text{H}_2\text{PO}_4^- + \tfrac{7}{5}\text{H}^+ + 14\text{H}_2\text{O}$$

$$7\text{CaHPO}_4.2\text{H}_2\text{O} + \tfrac{7}{3}\text{F}^- + \tfrac{14}{3}\text{Ca}^{2+} = \quad (3)$$

$$\frac{7}{3} Ca_5(PO_4)_3F + 7H+$$

Equation (1) corresponds to the treatment step in which DCPD is formed in the tissue. In the pH range to be employed, the Ca/P in the DCPD-forming solution is approximately ½. This is why its composition is represented as being $Ca(H_2PO_4)_2$. The second step, which converts DCPD to fluorapatite can be represented by equation (2) or (3) depending on whether a source of $Ca^{2+}$ ions is available (e.g., from saliva) during the reaction. It is seen from equations (1) through (3) that for each unit of hydroxyapatite initially consumed by the DCPD-forming solution, 7/5 to 7/3 units of fluorapatite will form. See, Chow, L. C. and Brown, W. E., "An approach to Remineralization via Saliva." *Foods, Nutritions, and Dental Health, Third Annual Conference*, 1979 (American Dental Association 1983). Therefore, the inventive fluoride treatment procedure is also a remineralization procedure. This is in contrast to the topical fluoride treatment methods presently in use which are, to some degree, demineralization procedures.

The present invention also provides compositions and methods for topically fluoridating and/or mineralizing dental tissue in a single step. As above, the inventive DCPD-forming solution or gel includes DCPD, DCPA, MCPM, or MCPA, or a combination thereof, with calcium and phosphate concentrations greater than or equal to approximately fifty percent of the saturation concentrations for the indicated phosphate compound(s) such that the pH of the solution or gel is less than or equal to the singular point pH of DCPD and hydroxyapatite, thus insuring that DCPD will form in the tooth surface. The inventive one-step DCPD-forming solution or gel also includes at least one complex fluoride compound that does not immediately release free fluoride ions into the aqueous solution or gel upon dissolution. Thus, large quantities of free fluoride ions are not released into the solution or gel and there is minimal precipitation of calcium fluoride. Rather, the complex fluoride compounds hydrolyze to release free fluoride ions as the pH of the solution or gel increases. Since the pH of the solution or gel gradually increases as DCPD is formed, the complex fluoride ions necessarily hydrolyze as DCPD is formed. As the fluoride concentration slowly rises due to hydrolysis, $CaF_2$ may begin to precipitate out of the solution or gel. Importantly, however, the calcium in the precipitated $CaF_2$ is not from the tissue, but rather from the DCPD-forming solution or gel. Thus, the inventive solution or gel does not dissolve tooth tissue; but instead, as described above, the amount of mineral in the tissue is actually increased. Therefore, the complex fluoride compounds replace conventional fluoridation agents as sources for free fluoride ions and allow the novel topical fluoridation and mineralization procedures to be condensed into a single step. This one-step solution or gel is preferably saturated with respect to fluorapatite or calcium fluoride in order to prevent the temporary removal of fluorapatite before the complex fluoride compounds hydrolyze and release free fluoride into the solution or gel.

The present invention additionally provides compositions and methods for topically fluoridating and/or mineralizing dental tissue using solid components that yield DCPD-forming solutions upon contact with dilute aqueous solvents, such as water or saliva. The surface of the tissue is treated with a substantially nonaqueous dispersion that contains either fluorapatite or $CaF_2$ and either MCPM or MCPA, the combination thereof being dispersed within a substantially nonaqueous medium. When this dispersion is placed on the tooth in the presence of a dilute aqueous solvent, an aqueous solution or gel is formed that contains calcium and phosphate in concentrations greater than or equal to half of the saturation concentration for DCPD. Unlike a solution formed from solid DCPD and water, the pH of the inventive solution is less than or equal to the singular point pH of DCPD and hydroxyapatite, which insures that DCPD forms in the tooth surface. Furthermore, the solution or gel that is formed is approximately saturated with respect to fluorapatite. The initial application of the DCPD-forming solids should preferably be followed by a standard fluoridation treatment such that fluorapatite is incorporated into the tissue. Alternatively, the sequence can be reversed so that $CaF_2$ is formed first in the tissue, which can later react with DCPD that is formed by treatment with a DCPD-forming solution. The two steps may also be performed simultaneously. These inventive solid compositions may be conveniently incorporated into substantially nonaqueous media such as toothpastes, chewing gums, or mouthrinses, or be stored as dry powder mixtures for use by patients at home.

Further advantages and embodiments of the present invention will become evident from the following description of the preferred embodiments and from the claims.

DESCRIPTION OF THE PREFERRED EMBODIMENTS

The DCPD-forming solutions or gels of the present invention may be easily prepared by a dentist in his office. For example, a solution saturated with respect to DCPD and fluorapatite may be formed by dissolving solid DCPD in a 0.02 to 1.2M solution of $H_3PO_4$ until the solution is saturated with respect to DCPD. The phosphoric acid is necessary to lower the pH of the resultant solution to 4.3 or less. Though phosphoric acid is preferred, other acids may be used to lower the pH of the solution into the required range so long as the acid does not interfere with the formation of DCPD in the tooth enamel. In order to saturate the solution with respect to fluorapatite or calcium floride, simple fluoride compounds, e.g., NaF, KF, $CaF_2$, $SnF_2$, or fluorapatite, should be added to the solution until precipitation is noted. The inventive solution should then be filtered in order to remove any undissolved solids. These solutions are usually stable for several months and may be prepared in advance or at the time of intended use.

Solutions saturated with respect to MCPM and/or MCPA may be prepared by dissolving the solid phosphate compound in a dilute $H_3PO_4$ solution having a concentration equal to or greater than 0.4M. Solutions that are saturated with respect to DCPD or DCPA and also with respect to MCPM or MCPA may be prepared by dissolving the desired pair of solids in distilled water until saturated. If a sufficient amount of MCPM and/or MCPA is present, no phosphoric or other acid need be added to bring the pH of the solution within the required range. The resulting solutions should then be filtered and simple fluoride compounds added.

The solutions or gels described above may also be made up to have saturation values between fifty and one hundred percent with respect to the phosphate compounds(s), i.e., DCPD, DCPA, MCPM, and/or MCPA. This undersaturation causes a slight etching on the surface of the tooth because a small amount of tooth enamel is dissolved. It has been suggested that slight etching may enhance the reactivity of the enamel, allowing a greater degree of mineralization or fluoridation. See, Aasenden, R. et al, "The Response of Intact and Experimentally Altered Human Enamel to Topical Fluoride." Archs. oral Biol. 13: 543–552 (1968). Etching of the surface enamel may also be desirable in conjunction with the application of polymeric coatings onto the tooth surface after topical fluoridation or mineralization treatments in order to fix the fluoride on the tooth surface. See, Richardson, B., "Fixation of Topically Applied Fluoride in Enamel," J. Dent. Res. 46 (Supp. 1): 87–91 (1967).

The inventive solutions without complex fluoride compounds should preferably be applied in a two-step procedure. First, the solution or gel saturated with respect to the calcium phosphate compound and either fluorapatite or $CaF_2$ should be applied to the surface of the dental enamel in a pretreatment step. The most effective DCPD-forming solutions have low pH's and high calcium and phosphate concentrations. However, some of these solutions have pH's at ambient temperatures that may be harmful to the soft tissues of the mouth if allowed to remain there for long periods of time, e.g., pH 2.1. Thus, these strong solutions should be applied by a dentist under clinical conditions by any of the conventional means well known in the dental art. Otherwise, mild DCPD-forming solutions or gels, e.g., $2.7 \leq pH \leq 4.3$ at ambient temperatures, may be incorporated into mouthrinses, toothpastes or chewing gums that could be applied by the patient at home. Additionally, the inventive solutions or gels may be incorporated into absorbent dental floss or tape that could be applied to the dental enamel.

Second, following pretreatment with the DCPD-forming solution, a conventional fluoridation agent should be applied to the pretreated enamel. It is preferable that the pretreated surface be rinsed before application of the fluoridation agent such that the DCPD-forming solution or gel is substantially removed from the surface of the dental enamel. Any conventional fluoridation agent may be used with the present invention, e.g., acidulated phosphate fluoride, $SnF_2$, NaF, or $TiF_4$. The fluoridation agent may be applied clinically, via conventional oral fluoride-release devices, by means of fluoride containing toothpastes, mouthrinses, or chewing gums, or by any other means that maintains a significant fluoride level within the mouth. In certain cases, a sufficient amount of fluoride may be obtained from the available drinking water, diet, or other means such that a special source of fluoride may become unnecessary.

COMPARATIVE EXAMPLE 1

Four extracted human molars, each having three separate exposed areas, were treated in the following manner. The first area was treated for five minutes with a solution saturated with respect to DCPD having a pH of 2.1. The second area was treated for five minutes with the samd DCPD solution that had been additionally saturated with respect to fluorapatite. The third area, which received no treatment, served as the control. After treatment, all four teeth were rinsed briefly in distilled water and then washed for seventeen hours in a 1.0M KOH solution saturated with respect to fluorapatite in order to remove any calcium fluoride that might have formed. See, Caslavska, V., et al, "Determination of Calcium Fluoride Formed from in vitro Exposure of Human Enamel to Fluoride Solutions." Archs. oral Biol. 20: 333–339 (1975). Three separate layers of enamel were then biopsied in each area of each tooth in order to determine the enamel fluoride content. The results are shown below in Table I.

TABLE I

| Mean Change in Enamel Fluoride Content (ppm) | | |
|---|---|---|
| Enamel layer thickness ($\mu$m) | Prior art DCPD solution | Inventive DCPD solution containing fluorapatite |
| $4.05_{(0.43)}$[1] | $-783_{(253)}$ | $+105_{(574)}$ |
| $4.28_{(0.31)}$ | $-474_{(309)}$ | $+47_{(252)}$ |
| $4.46_{(0.34)}$ | $-78_{(108)}$ | $-40_{(220)}$ |

As can be seen, the treatment with the prior art DCPD-forming solution that was not saturated with respect to fluorapatite removed a significant amount of fluoride from the enamel in all layers. By contrast, the inventive DCPD-forming solution saturated with respect to fluorapatite appears to have added fluoride to the enamel at all but the deepest layer, where a relatively small amount of fluoride was removed. Thus, the inventive solutions or gels are superior to the known DCPD-forming solutions or gels in that fluoride treatment need not immediately follow in order to prevent significant loss of native enamel fluoride.

The inventive method may be condensed into a single step procedure by adding complex fluoride compounds to the known DCPD-forming solutions or gels. Such solutions may be formed by taking the DCPD-forming solutions described above, with or without saturation with respect to fluorapatite or calcium fluoride, and dissolving one or more salts of complex fluoride acids into the solution or gel such that hydrolysis of the complex fluoride ions will yield free fluoride ions. Examples of complex fluoride acids that may be used in the present invention are $H_2SiF_6$, $HPF_6$, $HBF_4$, $HBF_3OH$, $H_3FeF_6$, and $H_2PO_3F$. Examples of their corresponding salts are $Na_2SiF_6$, $CaSiF_6$, $Ca(PF_6)_2$, $NaBF_4$, $NaBF_3OH$, $Na_3FeF_6$ and $Na_2PO_3F$. Numerous other complex fluoride ions are known in the chemical arts and may be used with the present invention. The properties of these ions vary to some extent (see, e.g., Ryss, I. G. et al, "The Kinetics and Mechanism of the Alkaline Hydrolysis of the Hydroxytrifluorobate Ion $BF_3OH$-". Russ. J. Phys. Chem. 41: 1544–1549 (1967); Clark, H. R. et al, "Ligand Substitution Catalysis via Hard Acid—Hard Base Interaction." J. Am. Chem. Soc. 92: 816–822 (1970)) and the relative effectiveness of each type of complex fluoride salt may be determined by routine experimentation.

The stability of the DCPD-forming solutions containing complex fluoride ions is desirably of the order of thirty minutes. Thus, the solution should be prepared fresh before each use. Similar to the two-step inventive DCPD-forming solution or gel, the one-step solution or gel containing complex fluoride ions may be undersaturated by as much as fifty percent with respect to the phosphate compound(s). This would cause slight etching on the surface of the enamel. Also, it is preferred that the DCPD-forming solution containing complex fluoride ions be saturated with respect to fluorapatite or calcium fluoride in order to prevent the removal of fluorapatite from the dental enamel. This is not essential, however, since the DCPD-forming solution will necessarily be followed by a fluoride treatment due to the hydrolysis of the complex fluoride ions.

EXAMPLE 2

Four areas delineated on each of three bovine teeth were treated for five minutes with one-step fluoridating solutions, each saturated with respect to DCPD and having a pH of 2.1. The first solution additionally contained $NaBF_3OH$ in a concentration of 0.1M, the second solution contained 0.48M $NaBF_4$ and the third solution contained 0.24M $CaSiF_6$. A fourth untreated area served as a control. All of the samples were washed with 1.0M KOH before measurement and four biopsies on each sample were taken. The results are tabulated below in Table II.

TABLE II

| | Mean Enamel Fluoride Contents (ppm) | | | |
|---|---|---|---|---|
| Enamel layer thickness ($\mu$m) | DCPD+ $NaBF_3OH$ | DCPD+ $NaBF_4$ | DCPD+ $CaSiF_6$ | Control |
| $3.29_{(0.74)}$[1] | $1195_{(218)}$ | $815_{(213)}$ | $2039_{(341)}$ | $818_{(665)}$ |
| $3.61_{(0.72)}$ | $1085_{(160)}$ | $753_{(193)}$ | $1996_{(503)}$ | $729_{(431)}$ |
| $4.14_{(0.69)}$ | $1040_{(243)}$ | $716_{(118)}$ | $1744_{(691)}$ | $726_{(317)}$ |
| $3.88_{(0.83)}$ | $1133_{(220)}$ | $636_{(178)}$ | $1607_{(742)}$ | $569_{(154)}$ |

[1]Quantities in parenthesis indicate standard deviations.

As can be seen from the above results, two of the three inventive one-step solutions containing complex fluoride compounds resulted in significant enamel fluoride uptake at all depths as compared to the control. $CaSiF_6$ was the most effective of the three complex fluoride compounds tested, while $NaBF_4$ showed the least fluoride uptake.

For use in substantially nonaqueous dispersions, MCPM and MCPA are highly advantageous because these two compounds when dissolved in dilute aqueous solvents produce DCPD-forming solutions having pH's below 4.3. This is in contrast to solid DCPD, which does not form a DCPD-forming solution when dissolved in a dilute aqueous solvent. See Pickel et al, "The Effects of a Chewing Gum Containing Dicalcium Phosphate on Salivary Calcium and Phosphate." J. Ala. Med. 2: 286-287 (1965). To form the inventive dispersions, solid fluorapatite and either MCPA or MCPM, or both, also in solid form, are mixed together. Preferably, the solid compounds are dispersed within a substantially nonaqueous medium, such as substantially nonaqueous toothpaste, chewing gum, or mouthrinse. Upon contact with a dilute aqueous solvent, such as water or saliva, an aqueous solution or gel is formed that contains calcium and phosphate in concentrations greater than or equal to approximately fifty percent of the saturation concentrations for DCPD such that the pH of the solution or gel is less than or equal to the singular point pH of DCPD and hydroxyapatite, insuring that DCPD will form in the enamel's surface. Furthermore, the resulting solution or gel is also saturated with respect to fluorapatite such that no fluorapatite is dissolved from the tooth enamel, even if pretreatment is not immediately followed by a conventional fluoridation treatment. The solid components may be dispersed within the various substantially nonaqueous media, such as substantially nonaqueous toothpaste, chewing gum, or mouthrinse, in manners well known in those particular arts. In addition, the substantially nonaqueous dispersion may be bonded to dental floss or tape in manners well known in those particular arts. Alternatively, the solid components could be mixed together without any nonaqueous media to form the inventive dispersion.

DCPD, DCPA and/or $CaF_2$ may also be added in solid form to the inventive nonaqueous dispersion, in addition to MCPM or MCPA, as long as the resulting solution or gel does not have a pH greater than 4.3 at ambient temperatures. Treatment with the nonaqueous dispersion should be followed with a conventional fluoridation treatment as above described. In addition, the inventive nonaqueous dispersions or dry powder mixtures may contain complex fluoride compounds similar to those described for single-step treatment procedures.

In addition to the essential constituents of the inventive solutions or gels, additional components may be added as necessary to obtained desired calcium and phosphate concentrations, pH's, ionic strengths, or viscosities. These would include acids, bases, salts, or thickening agents, which are all well known in the art of dental materials.

Though the preferred embodiments of the present invention have been described in terms of the fluoridation and mineralization of dental enamel, the inventive methods and compositions are also useful in treating dentin and exposed root surfaces. Under ordinary circumstances neither of these dental tissues is exposed. However, dentin may become exposed if the overlying enamel is abraded and gingival recession may expose the root surfaces. In such cases, treatment with the inventive compositions and methods would reduce the incidence of caries as well as the temperature, pressure, chemical, and mechanical sensitivities of these tissues. It should also be understood that the foregoing disclosure emphasizes certain specific embodiments of the invention and that all modifications or alternatives equivalent thereto fall within the spirit or scope of the invention.

We hereby claim as our invention:

1. A method for topically fluoridating and/or mineralizing dental tissue such that $Ca_5(PO_4)_3$ is incorporated into the tissue, comprising in combination the following steps:
    (a) treating the surface of the tissue with a substantially nonaqueous dispersion such that $CaHPO_4.2H_2O$ is formed in the surface of the tissue, the dispersion containing (1) $Ca_5(PO_4)_3F$ and (2) at least one calcium phosphate compound selected from the group consisting of $Ca(H_2PO_4)_2.H_2O$ and $Ca(H_2PO_4)_2$, the treatment step occurring in the presence of a dilute aqueous solvent such that the dispersion and the solvent form an aqueous solution or gel containing calcium and phosphate ions in concentrations greater than or equal to approximately fifty percent of the saturation concentration for $CaHPO_4.2H_2O$ in the solution or gel, the solution or gel being saturated with respect to $Ca_5(PO_4)_3F$, and the solution or gel having a pH less then or equal to approximately 4.3; and
    (b) applying a fluoridation agent selected from the group consisting of acidulated phosphate fluoride, $SnF_2$, NaF and $TiF_4$ to the surface of the tissue.

2. The method of claim 1 wherein the phosphate compound is $Ca(H_2PO_4)_2.H_2O$.

3. The method of claim 1 wherein the dilute aqueous solvent is saliva.

4. The method of claim 1 wherein the substantially nonaqueous dispersion additionally comprises at least one compound selected from the group consisting of $CaHPO_4.2H_2O$, $CaHPO_4$, and $CaF_2$.

5. A substantially nonaqueous dispersion for topically fluoridating and/or mineralizing dental tissue, comprising (1) $Ca_5(PO_4)_3F$ and (2) at least one calcium phosphate compound selected from the group consisting of $Ca(H_2PO_4)_2.H_2O$ and $Ca(H_2PO_4)_2$, such that $CaHPO_4.2H_2O$ is formed in the surface of the tissue when the surface of the tissue is treated with the dispersion in the presence of a dilute aqueous solvent.

6. The dispersion of claim 5 wherein the phosphate compound is $Ca(H_2PO_4)_2.H_2O$.

7. The dispersion of claim 5 additionally comprising at least one compound selected from the group consisting of $CaHPO_4.2H_2O$, $CaHPO_4$, and $CaF_2$.

* * * * *

UNITED STATES PATENT AND TRADEMARK OFFICE
CERTIFICATE OF CORRECTION

PATENT NO. : 4,556,561
DATED : December 3, 1985
INVENTOR(S) : Walter E. Brown and Laurence C. Chow It is certified that error appears in the above-identified patent and that said Letters Patent is hereby corrected as shown below:

Column 1,
Line 6, please add the following language as paragraph one:

-- This invention was supported in part by research grant number DE05354 to the American Dental Association Health Foundation from the National Institute of Dental Research. The Government has certain rights in this invention. --

Signed and Sealed this

Fourth Day of March, 2003

JAMES E. ROGAN
*Director of the United States Patent and Trademark Office*